(12) United States Patent
Loncar

(10) Patent No.: US 7,146,980 B2
(45) Date of Patent: Dec. 12, 2006

(54) TUBE FOR USE IN AN ANESTHETIC SYSTEM

(75) Inventor: Mario Loncar, Ekerö (SE)

(73) Assignee: Maquet Critical Care AB, Solna (SE)

( * ) Notice: Subject to any disclaimer, the term of this patent is extended or adjusted under 35 U.S.C. 154(b) by 263 days.

(21) Appl. No.: 10/714,209

(22) Filed: Nov. 14, 2003

(65) Prior Publication Data

US 2004/0103898 A1 Jun. 3, 2004

(30) Foreign Application Priority Data

Nov. 28, 2002 (SE) .................................. 0203518

(51) Int. Cl.
*A62B 7/10* (2006.01)
*A61M 16/00* (2006.01)
*B01D 53/02* (2006.01)

(52) U.S. Cl. ..................... 128/205.28; 128/203.12; 128/205.27; 96/154

(58) Field of Classification Search ........... 128/203.12, 128/203.13, 203.14, 204.18, 205.12, 205.27, 128/205.28, 205.29, 910, 911, 912, 914; 95/900, 901, 902, 139; 96/108, 121, 153, 96/154; 55/478, 490, DIG. 32
See application file for complete search history.

(56) References Cited

U.S. PATENT DOCUMENTS

| | | | |
|---|---|---|---|
| 2,677,371 A * | 5/1954 | Loredo Serra | 128/205.12 |
| 3,867,294 A * | 2/1975 | Pall et al. | 210/489 |
| 4,285,699 A | 8/1981 | Itoh | |
| 4,627,431 A | 12/1986 | Werjefelt | |
| 4,883,051 A * | 11/1989 | Westenskow et al. | 128/204.21 |
| 5,044,361 A * | 9/1991 | Werner et al. | 128/204.16 |
| 5,320,093 A * | 6/1994 | Raemer | 128/203.12 |
| 5,360,002 A | 11/1994 | Smith | |
| 5,471,979 A | 12/1995 | Psaros et al. | |
| 5,546,930 A * | 8/1996 | Wikefeldt | 128/201.13 |
| 6,152,133 A | 11/2000 | Psaros et al. | |
| 6,397,842 B1 * | 6/2002 | Lee | 128/203.26 |
| 6,550,622 B1 * | 4/2003 | Koslow | 210/490 |
| 6,745,771 B1 * | 6/2004 | Castor et al. | 128/205.27 |
| 2002/0002976 A1 | 1/2002 | Smith et al. | |

FOREIGN PATENT DOCUMENTS

| | | |
|---|---|---|
| EP | 0 238 463 | 9/1987 |
| FR | 2 150 024 | 3/1973 |
| GB | 511055 | 8/1939 |
| GB | 1 485 458 | 9/1977 |
| GB | 2 376 185 | 12/2002 |

OTHER PUBLICATIONS

Patent Abstracts of Japan, vol. 017, No. 693 (C1144) for Japanese Application 5-236936.

* cited by examiner

*Primary Examiner*—Teena Mitchell
(74) *Attorney, Agent, or Firm*—Schiff Hardin LLP

(57) ABSTRACT

A tube for use in an anesthetic system has an essentially cylindrical housing. More effective take-up of carbon dioxide is achieved by an absorbent for carbon dioxide that is arranged within the tube.

7 Claims, 2 Drawing Sheets

TUBE FOR USE IN AN ANESTHETIC SYSTEM

BACKGROUND OF THE INVENTION

1. Field of the Invention

The present invention relates to a tube suitable for use in an anesthetic system as well as a tubing system and an anesthetic system.

2. Description of the Prior Art

Anesthetic systems described in, inter alia, U.S. Pat. Nos. 5,471,979 and 6,152,133 employ a unit for adsorption and desorption of gaseous anesthetic, arranged in a tubing system coupled to an anesthetic apparatus. This results in a large saving in the amount of anesthetic that is required for each patient.

However, the unit occupies a certain volume that with every breath fills with exhaled gas. This exhaled gas also includes carbon dioxide that with every inspiration also is returned to the patient.

Moreover, the choice of material used in the unit (for adsorption and desorption) can influence the amount of carbon dioxide that is returned since certain materials adsorb and desorb carbon dioxide apart from anesthetic.

Therefore, it is known to provide anesthetic systems of this type with an absorber unit for carbon dioxide in the inspiration branch of the tubing system (downstream of the unit for adsorption and desorption of gaseous anesthetic).

Even though this absorber unit does not need to retain the same volume of adsorbent as an absorber in a conventional anesthetic circle system (where all exhaled carbon dioxide is to be absorbed), it still has a volume that influences the system.

One problem with such an absorber unit is that it must still occupy a certain volume in order for the absorbent to be able to absorb all of the carbon dioxide. If this does not occur, measurement spikes may arise in a capnogram during inspiration. (Conversely, the volume is normally not of such a size that the patient is notably influenced).

A further problem with such an extra volume in the inspiration branch is that a rapid regulation of the anesthetic concentration may be complicated.

SUMMARY OF THE INVENTION

An aim of the present invention is to provide a solution to the aforementioned problems.

The above object is achieved in accordance with the invention in a tube for use in an anesthetic system, the tube having an essentially cylindrical housing, and an absorber for carbon dioxide disposed within the tube, occupying a portion of the cross-sectional area of the tube.

By integrating the absorbent with a tube in this manner a large contact area between flowing gas and the absorbent is achieved at the same time as the added volume is minimized. Since the absorbent occupies only a portion of the cross-sectional area, there will be significant part of the tube that provides an unhindered flow path for the breathing gas. Flow resistance can even be kept to a minimum by forming the tube such that the unhindered flow path obtains the same size as the rest of the flow paths for the breathing gas. The absorbent may be arranged in the tube in many different ways.

The object also is achieved according to the invention in a tubing system employing such a tube and in an anesthetic system having a tubing system with such a tube.

DESCRIPTION OF THE PREFERRED EMBODIMENTS

Figure 1:
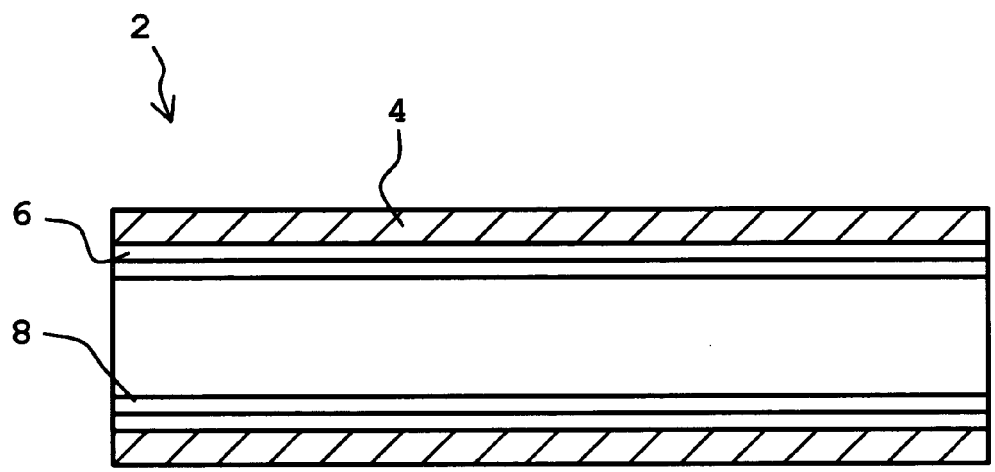
FIG. 1 is a schematic illustration of a first embodiment of a tube according to the invention.

A first embodiment of a tube 2 according to the invention is shown in FIG. 1. The tube 2 has a housing 4 that, as in normal tubes, is cylindrical. An absorbent 6 for carbon dioxide is arranged internal the housing 4, against its inner wall. A membrane 8 is arranged inside of the absorbent 6. The membrane 8 is permeable to carbon dioxide. It should be noted that the relative thicknesses of the housing 4, the absorbent 6 and the membrane 8 are not shown in their correct proportions in the FIG. 1.

Since the absorbent 6 occupies only a portion of the cross-sectional area of the tube 2, the interior of the tube 2 may easily be made so that the absorbent 6 provides no or only a small resistance to flow without impeding its efficiency in absorbing carbon dioxide.

Carbon dioxide in a breathing gas passing through the pipe will diffuse through the membrane 8 and be absorbed in the absorbent 6. By the tube 2 being stretched the adsorption of carbon dioxide can occur over a longer time interval than would be possible with the same volume of absorbent collected in a container.

The tube 2 may in principle be so long as to form the entire inspiration branch of a tubing system of an anesthetic system (described in more detail in connection with FIG. 3).

The absorbent 6 and the membrane 8 are, in the first embodiment, also cylindrical. This is, however, not essential. The absorbent 6 alternatively may be placed over only a portion of the inner surface of the housing 4. There could even be a number of absorbents along the inner surface.

Figure 2:
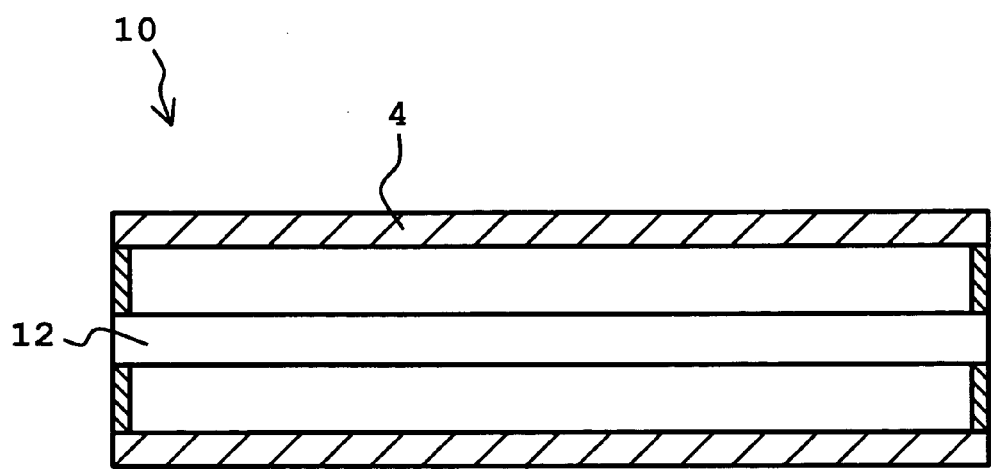
FIG. 2 is a schematic illustration of a second embodiment of a tube according to the invention.

A second embodiment of the invention is shown in FIG. 2 in the form of a tube 10. The tube 10, in common with the foregoing embodiment, is provided with a housing 4 that can be identical to the foregoing and is therefore given the same reference numeral. A cylindrical absorbent 12 is, in this case, suspended in the middle of the of the tube 10 flow path in a suitable manner using stays, a mesh or other means.

A flowing gas usually has a velocity profile that is fastest in the middle of a pipe and is slowest at its walls. This placement therefore results in the absorbent 12 coming into faster and more direct contact with the carbon dioxide in the gas. Moreover, the absorbent 12 creates turbulence that in turn increases the contact between the carbon dioxide in the gas and the absorbent 12.

Again, the absorbent 12 occupies only a portion of the cross-sectional area of the tube 10. The flow-through area around the absorbent 12 can readily be as large as in other sections of the flow pathways of a tubing system (as discussed in connection with FIG. 3).

Also in this case there may be a number of absorbents 12 positioned after each other in the middle of the flow path of the tube 10.

It should be noted that the absorbent 12 (likewise the absorbent 6) may be formed of any carbon dioxide absorbing material. It is, however, advantageous to select a material having as high an absorbtion capacity per unit volume as possible.

A combination of the two embodiments is also possible, with the absorbent being placed both in the middle of the housing and along the inner walls.

Figure 3:
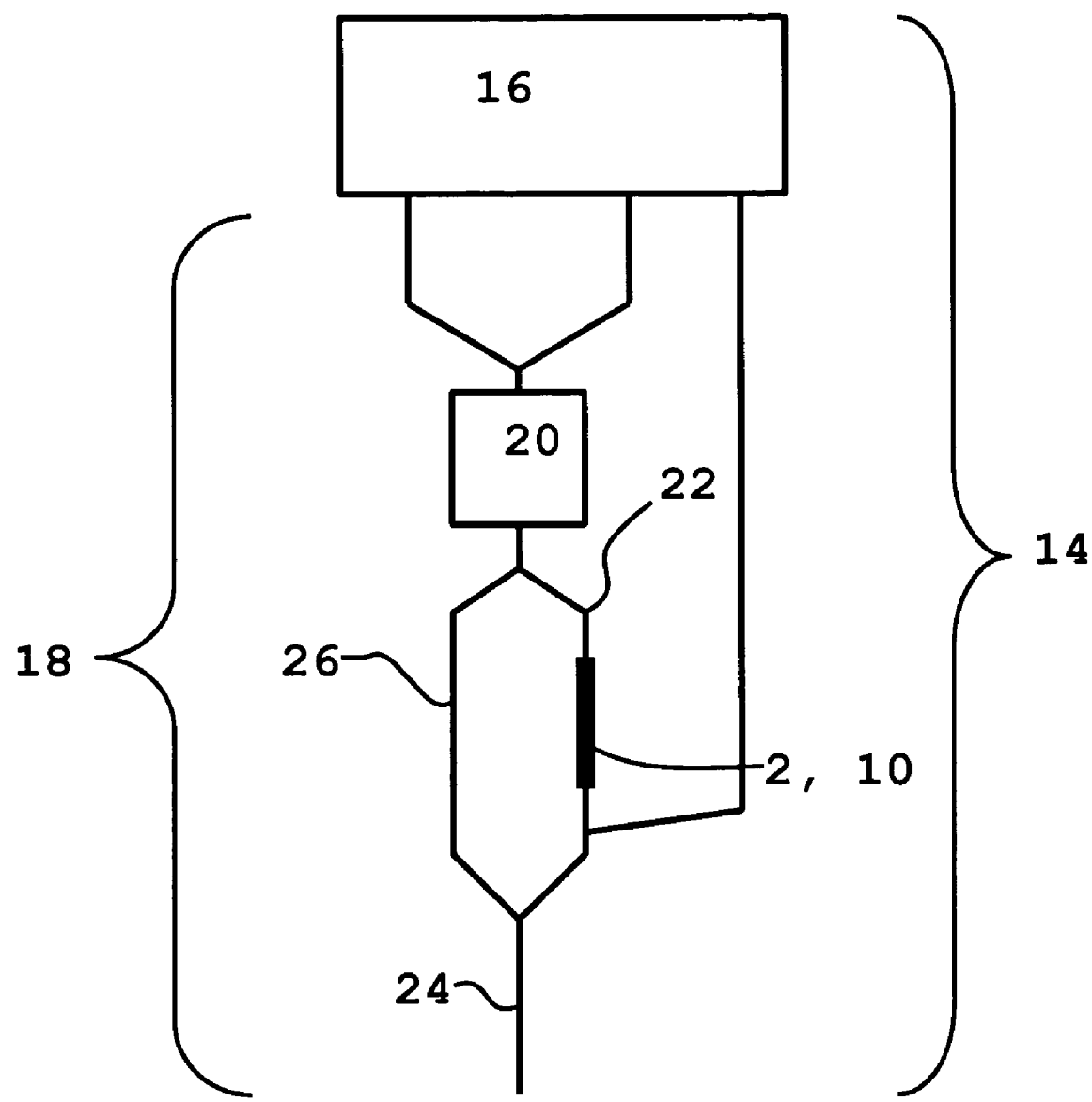
FIG. 3 is a schematic illustration of an embodiment of an anesthetic system and tubing system according to the invention.

An anesthetic system 14 according to the invention is shown schematically in FIG. 3. The anesthetic system 14 has an anesthetic apparatus 16 and a tubing system 18 according to the invention.

The tubing system 18 has, inter alia, a unit 20 for the adsorption and desorption of gaseous anesthetic; an inspiration branch 22; a patient connection 24; and an expiration branch 26. A tube 2, 10 according to a one of FIGS. 1 and 2 is arranged in the inspiration branch 22 in order to absorb carbon dioxide. Notably, the open flow through area in the tube 2, 10 can readily be made coherent with the rest of the tubing system 18, especially the rest of the inspiration branch 22. This means that the absorbent 6, 12 will essentially provide no or only a small addition to the overall flow resistance of the tubing system 18.

It is also feasible to shape the tube 2, 10 so it forms the entire inspiration branch 22. the absorbent 6, 12 (or a number of absorbents) then could be evenly distributed throughout the entire length of the tube 2, 10.

For further details concerning the anesthetic apparatus 14 or the tubing system 18 reference is made to the earlier mentioned U.S. Pat. Nos. 5,471,979 and 6,152,133.

Although modifications and changes may be suggested by those skilled in the art, it is the intention of the inventor to embody within the patent warranted hereon all changes and modifications as reasonably and properly come within the scope of his contribution to the art.

I claim as my invention:

1. A tube for use in an anesthetic system, said tube comprising:
    a substantially cylindrical housing having a cross-sectional area adapted for gas flow therethrough; and
    an absorber for carbon dioxide disposed inside said housing and only occupying a portion of said cross-sectional area of said housing and having a surface facing said gas flow disposed to allow interaction of said absorber with said gas flow to adsorb carbon dioxide from said gas flow, while presenting substantially no impediment to said gas flow.

2. A tube as claimed in claim 1 wherein said housing has an interior surface, and wherein said absorber is disposed against said interior surface.

3. A tube as claimed in claim 1 wherein said absorber has a substantially hollow cylindrical shape.

4. A tube as claimed in claim 1 wherein said absorber has a substantially cylindrical shape and is disposed in a center of said housing coaxial with said housing.

5. A tube as claimed in claim 1 wherein said housing surrounds an interior space in said housing, and wherein said tube comprises a membrane disposed to separate said absorber from direct contact with said interior space, said membrane being permeable to carbon dioxide.

6. A tubing system for use in an anesthetic system, said tubing system comprising:
    a unit for adsorption and desorption of gaseous anesthetic;
    an inspiration branch disposed downstream of said unit for adsorption and desorption of gaseous anesthetic, said inspiration branch comprising a tube having a substantially cylindrical housing with a cross-sectional area adapted for gas flow of a gas comprising said gaseous anesthetic therethrough
    an adsorber for carbon dioxide disposed within said tube, and occupying only a portion of said cross-sectional area of said housing and having a surface facing said gas flow disposed to allow interaction of said absorber with said gas flow to adsorb carbon dioxide from said gas flow, while presenting substantially no impediment to said gas flow.

7. An anesthetic system comprising:
    an anesthetic apparatus and a tubing system adapted to deliver gaseous anesthetic to a respirating subject;
    said tubing system having a unit for adsorption and desorption of gaseous anesthetic and an inspiration branch disposed downstream of said unit for adsorption and desorption of gaseous anesthetic;
    said inspiration branch comprising a tube having a substantially cylindrical housing with a cross-sectional area adapted for gas flow of a gas comprising said gaseous anesthetic therethrough; and
    an absorber for carbon dioxide disposed within said tube, and occupying only a portion of said cross-sectional area of said housing and having a surface facing said gas flow disposed to allow interaction of said absorber with said gas flow to adsorb carbon dioxide from said gas flow, while presenting substantially no impediment to said gas flow.

* * * * *